US007903861B2

(12) United States Patent
Luo et al.

(10) Patent No.: US 7,903,861 B2
(45) Date of Patent: Mar. 8, 2011

(54) METHOD FOR CLASSIFYING BREAST TISSUE DENSITY USING COMPUTED IMAGE FEATURES

(75) Inventors: Hui Luo, Rochester, NY (US); Lynn M. Fletcher-Heath, Rochester, NY (US); Lori L. Barski, Mendon, NY (US)

(73) Assignee: Carestream Health, Inc., Rochester, NY (US)

( * ) Notice: Subject to any disclaimer, the term of this patent is extended or adjusted under 35 U.S.C. 154(b) by 1049 days.

(21) Appl. No.: 11/616,953

(22) Filed: Dec. 28, 2006

(65) Prior Publication Data

US 2008/0159613 A1 Jul. 3, 2008

(51) Int. Cl.
*G06K 9/00* (2006.01)
(52) U.S. Cl. .......................... 382/132; 382/128
(58) Field of Classification Search .................. 382/128, 382/132
See application file for complete search history.

(56) References Cited

U.S. PATENT DOCUMENTS

| 6,985,558 | B1 * | 1/2006 | Russell ........................ 378/162 |
| 7,664,604 | B1 * | 2/2010 | Heine et al. ..................... 702/19 |
| 2003/0174873 | A1 | 9/2003 | Giger et al. |
| 2004/0008901 | A1 | 1/2004 | Avinash |
| 2005/0018893 | A1 | 1/2005 | Wang et al. |
| 2006/0104532 | A1 | 5/2006 | Messina et al. |
| 2007/0274585 | A1 * | 11/2007 | Zhang et al. ................... 382/132 |

OTHER PUBLICATIONS

Byng et al. "Automated analysis of mammographic densities" Phys. Med. Biol. 41, pp. 909-923, 1996 ("Byng"), retrieved from http://iopscience.iop.org/0031-9155/41/5/007.*
Oliver et al, "Automatic classification of breast density" ICIP 2005. IEEE International Conference on Image Processing, Sep. 2005, pp. 1258-1261.*
Keir Bovis et al., Classification of Mammographic Breast Density Using A Combined Classifier Paradigm, International Workshop on Digital Mammography, pp. 177-180, 2002.
J.W. Byng et al., The Quantitative Analysis of Mammographic Densities, Phys. Med. Biol., vol. 39, pp. 1629-1638, 1994.
Styliani Petroudi et al., Automatic Classification of Mammographic Parenchymal Patterns: A Statistical Approach, Proceedings of the 25th Annual International Conference of the IEEE EMBS, Cancun, Mexico, Sep. 17-21, 2003., pp. 798-801, 2003.
Chuan Zhou et al., Computerized Image Analysis: Estimation of Breast Density on Mammograms, Med. Phys., vol. 28, pp. 1056-1069, 2001.
Lori L. Barski et al., New Automatic Tone Scale Mthod for Computed Radiography, SPIE Conference on Image Display, San Diego, CA 1998, pp. 164-178.
Punam Saha et al., Breast Tissue Density Quantification Via Digitized Mammograms, IEEE Transactions on Medical Imaging, vol. 20, No. 8, Aug. 2001.
Hui Li et al., "Computerized Analysis of Mammographic Parenchymal Patterns for Assessing Breast Cancer Risk: Effect or ROI Size and Location," Medical Physics, AIP vol. 31, No. 3, Mar. 2004, pp. 549-555, XP012074804.

* cited by examiner

*Primary Examiner* — Bhavesh M Mehta
*Assistant Examiner* — Stephen R Koziol

(57) ABSTRACT

A method for classifying tissue density of a breast includes obtaining mammography image data and segmenting the mammography image to identify the region representing the breast tissue. A plurality of regions within the breast tissue region are identified for obtaining image features therefrom. A plurality of image features are computed from the identified plurality of regions. The breast tissue density is classified using the computed plurality of image features.

14 Claims, 8 Drawing Sheets

|      | I   | II  | III |
|------|-----|-----|-----|
| LMLO | 0.2 | 0.7 | 0.1 |
| LCC  | 0.1 | 0.8 | 0.5 |
| RMLO | 0.3 | 0.9 | 0.1 |
| RCC  | 0.7 | 0.6 | 0.5 |
| Total| 1.3 | 3.0 | 1.2 |

*FIG. 8*

METHOD FOR CLASSIFYING BREAST TISSUE DENSITY USING COMPUTED IMAGE FEATURES

FIELD OF THE INVENTION

The invention relates generally to techniques for processing mammogram images, and in particular, to a method for automatically classifying breast density in mammograms to optimize image rendering and assist diagnosis.

BACKGROUND OF THE INVENTION

Screening mammography is a known method for detecting early signs of breast cancer in women. Generally, women undergo an X-ray exam in which X-ray films of the breast are exposed and then developed for review. A radiologist reads the films and assesses the likelihood of the presence of signs of breast cancer. If a suspicious finding is present, the woman will typically be invited for additional, more detailed diagnostic X-ray exams, followed by ultrasonic exams, and possibly biopsy.

In a typical screening exam in the United States of America, four X-rays of the breast are obtained. In conventional practice, two mammographic views are obtained for each breast: a cranio-caudal (CC) view is obtained by positioning the X-ray film horizontally under the compressed breast, and a medio-lateral oblique (MLO) view is obtained by positioning the X-ray film in a plane that is approximately orthogonal to the left-right axis. In some situations, more or fewer X-ray views may be obtained. The four views are typically labeled LCC (Left Cranio-Caudal), RCC (Right Cranio-Caudal), LMLO (Left Medio-Lateral Oblique) and RMLO (Right Medio-Lateral Oblique).

One goal of image processing of mammography images is to provide an optimal rendering of breast tissue for the diagnostician. Image data that is initially analyzed and used for this purpose can include detection of the different areas of the image data, for example: direct exposure areas, collimation areas, markers, and anatomy. An optimal tone scale can be calculated and used for display, based on characteristics of the anatomy area. For example, see Barski et. al., "New Automatic tone scale method for computed radiography," *Proc. SPIE*, 3335, 164-178, 1998. Further, mammography has specific requirements regarding the appropriate display of different tissue consistencies or densities. Analysis and classification of breast density based on the breast appearance within the digital image data can provide additional information such that an optimal rendering of each mammography image can be displayed.

FIG. 1 shows four exemplary unprocessed digital views of a mammogram taken during a typical screening exam. A display 10 includes an RMLO image 20, an LMLO image 30, an RCC image 40, and an LCC image 50 arranged as shown. Each image typically has a corresponding marker 12, placed by the technician nearest the axilla of the patient prior to imaging.

Breast density has been acknowledged to be a factor in effective mammogram interpretation. For example, there is a consideration that mammographic imaging techniques are less successful with denser breast tissue than with predominantly fat tissue. Fibro-glandular tissue in the breast tends to attenuate x-rays to a greater degree than does fat tissue, leading to increased difficulty in detection of cancer sites for denser breasts. As a guideline for classification, the American College of Radiology (ACR) Breast Imaging Reporting and Data System (BIRADS) has identified four major groupings for breast tissue density. Class I corresponds to breasts having high concentration of fat tissue. The Class II grouping indicates scattered fibroglandular densities. Class III indicates heterogeneously dense tissue. Class IV corresponds to extremely high breast density.

Various methods have been used for evaluation of breast density in mammograms. For example, Byng et al. in an article entitled "The Quantitative analysis of mammographic densities", *Phys. Med. Biol.* 39, 1994, discloses a method for quantifying the breast density using an interactive thresholding technique, which assesses the proportion of the mammographic image that represents dense tissue. Zhou et. al. in "Computerized image analysis: Estimation of breast density on mammograms", *Medical Physics,* 28 (6) 2001) describes a method for estimating mammographic breast density by using rule-based classification on the image gray-level histogram. Saha et al. in an article entitled "Breast tissue density quantification via digitized mammograms", *IEEE Transactions on Medical Imaging,* Vol. 20, No. 8, 2001) describes a method to segment dense tissue regions from fat within breasts from mammograms using scale-based fuzzy connectivity methods; then, different measures for characterizing mammography density are computed from the segmented regions. Bovis et al. in "Classification of Mammographic Breast Density Using a Combined Classifier Paradigm", *International Workshop on Digital Mammography*, p 177-180, 2002) investigated texture-based discrimination between fatty and dense breast types from the construction of spatial gray-level dependency matrices. Recently, Petroudi et al. in "Automatic Classification of Mammographic Patenchymal Patterns: A Statistical Approach", *IEEE Engineering in Medicine and Biology Society*, vol. 2, p 416-423, 2003) used textons to capture the mammographic appearance within the breast area.

While these approaches address the breast density classification problem, there remains a need for improvement in automated techniques for density classification. More accurate classification results, for example, can help to optimize image display for the diagnosing physician. An incremental improvements in tissue assessment and classification can result in increased accuracy of detection in using mammography.

SUMMARY OF THE INVENTION

One object of the present invention is to provide an automated method for classifying breast density in mammograms to assist mammogram image rendering and diagnosis.

Another object of the present invention is to provide a method for assigning a breast density type to mammograms of an examination.

According to one aspect of the present invention, there is provided a method for classifying tissue density of a breast. The method includes the steps of: accessing mammography image data of the breast; segmenting the mammography image to identify a breast tissue region representing the breast tissue; identifying a plurality of regions of interest within the breast tissue region for obtaining image features therefrom; computing a plurality of image features from the identified plurality of regions of interest; and classifying the tissue density of the breast using the computed plurality of image features.

In one embodiment of the present invention, the method includes extracting the breast region from mammogram images, and determining features capable of distinguishing the breast density as one of a set of predefined breast types.

BRIEF DESCRIPTION OF THE DRAWINGS

The foregoing and other objects, features, and advantages of the invention will be apparent from the following more particular description of embodiments of the invention, as illustrated in the accompanying drawings. The elements of the drawings are not necessarily to scale relative to each other.

FIG. 8 shows probability vectors for a set of images for a patient and combining values for tissue classification.

DETAILED DESCRIPTION OF THE INVENTION

Figure 1:
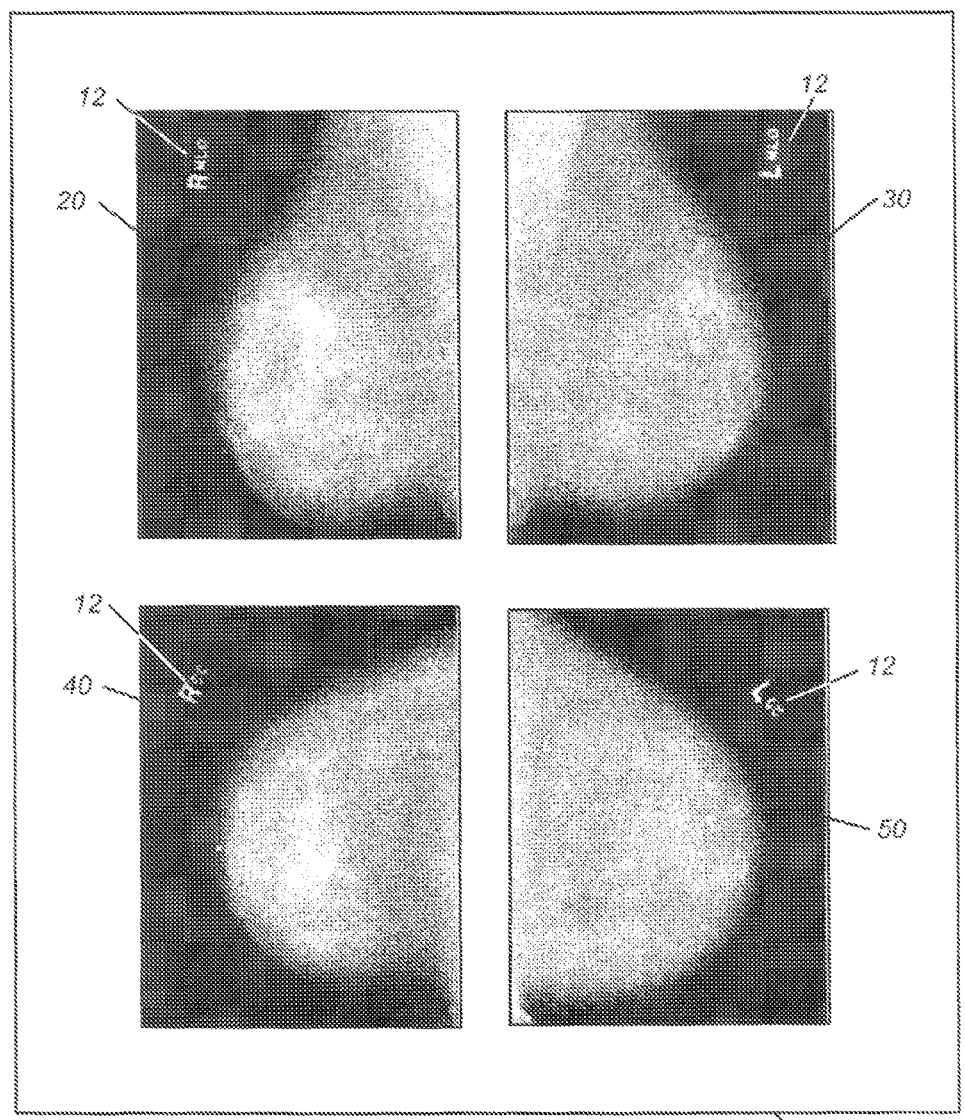
FIG. 1 shows a prior art exemplary group of four unprocessed images of a typical mammography screening exam.

The following is a detailed description of the preferred embodiments of the invention, reference being made to the drawings in which the same reference numerals identify the same elements of structure in each of the several figures.

Figure 2:
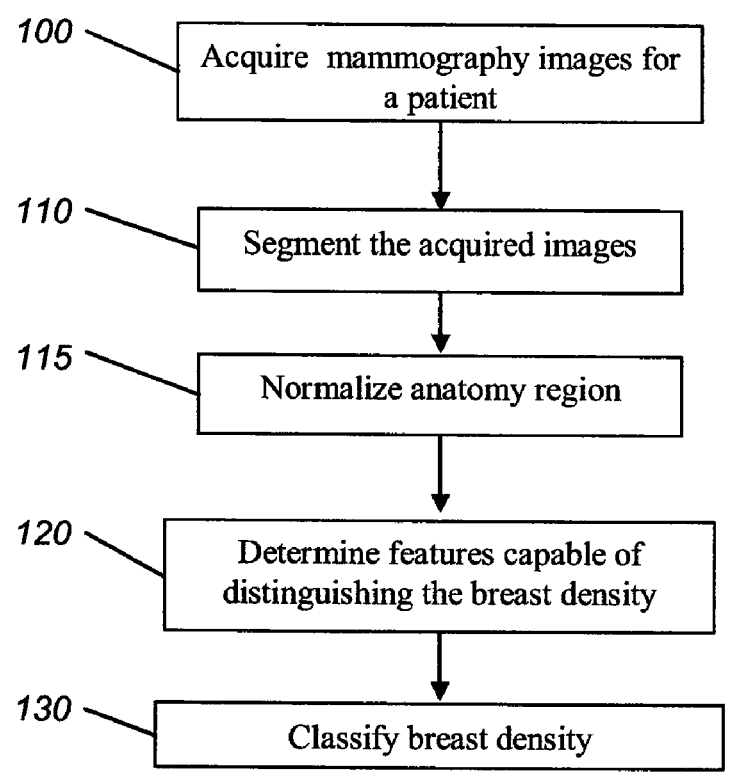
FIG. 2 shows a logic flow diagram illustrating steps in the automated method for classifying the breast density.

The present invention is directed to a method for automatically classifying the breast density of mammograms for image rendering and diagnosis. FIG. 2 shows a logic flow generally illustrating an automated method according to the present invention. As shown in FIG. 2, the method includes acquiring/accessing mammogram images of a patient in digital form (step 100); segmenting the breast region from the input mammogram images (step 110); normalizing the anatomy region (step 115); determining features capable of distinguishing the breast density from the segmented breast region (step 120), and classifying the breast density (step 130). These steps will be more particularly describe below.

In image acquisition step 100, mammography images of a patient are accessed/obtained as digital data. This digital data can be image data generated by digitizing an image or obtained directly, for example, by scanning film, from computed radiography (CR), or from digital radiography (DR).

Segmentation step 110 is executed to segment the mammography images into regions, for example three regions. A collimation region (i.e., foreground) is the area of the image that is occluded by X-ray collimation during the exposure and normally presents salient borders surrounding the body part. Direct exposure regions (i.e., background) are areas that have received direct X-ray exposure. Diagnosis useful regions (i.e., anatomy) contain the breast region and the marker region.

Segmentation techniques are known to those skilled in the medical imaging arts, and such techniques can be applied in step 110. For example, a method outlined in commonly assigned U.S. patent application No. 2005/0018893 entitled "Method of Segmenting a Radiographic Image into Diagnostically Relevant and Diagnostically Irrelevant Regions" by Wang et al., incorporated herein by reference, can be employed. Other segmentation techniques may obtain two thresholds from the image histogram, then segment the image into the foreground, background, and anatomy regions based on these thresholds.

Once an image is segmented, a processed image is generated by the following steps. First, the foreground and background areas are removed from the original mammogram image by setting their pixel values to a pre-defined value. Then, a region labeling method is executed on the anatomy region to identify the breast region and remove the marker and image noise. As a result of these operations, it is desired that the processed image contains solely the breast region.

An image intensity normalization step 115 is performed over the processed image to compensate for differences in exposure densities caused by patient variations and examination conditions. One technique to achieve normalization is to detect minimum and maximum brightness values from pixels in the anatomy region, then apply a linear or log transfer function to adjust the image brightness into a pre-defined range. Histogram equalization could be further performed on the image to spread out corresponding peaks in the image histogram so that more detail can be shown in low-contrast regions of the image. It is noted that the present invention is not limited to using the above method to normalize the image. Algorithms of similar nature can be employed to generate a consistent intensity and contrast image for subsequent processing.

Figure 3:
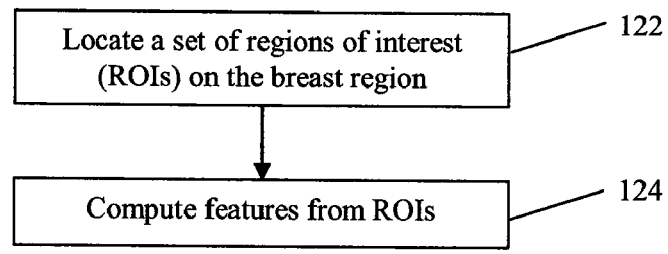
FIG. 3 is a logic flow diagram showing substeps of feature identification.

At step 120, features capable of distinguishing the breast density from the segmented breast region are determined. Regarding features identification step 120, FIG. 3 shows a logic flow diagram that includes two substeps. A ROI (Region of Interest) identification step 122 is executed for locating a set of ROIs that are used for sampling the breast tissue. Then, a features computation step 124 is implemented to capture the tissue characteristics for classification.

In ROI identification step 122, the assignment of ROIs satisfies a requirement that all ROIs are located within the breast region. Otherwise, the extracted features from the ROIs may not faithfully represent the characteristics of the breast tissues. Except for this requirement, the method of the present invention imposes no particular restrictions on the specific location of each ROI in the breast region.

Figure 4:
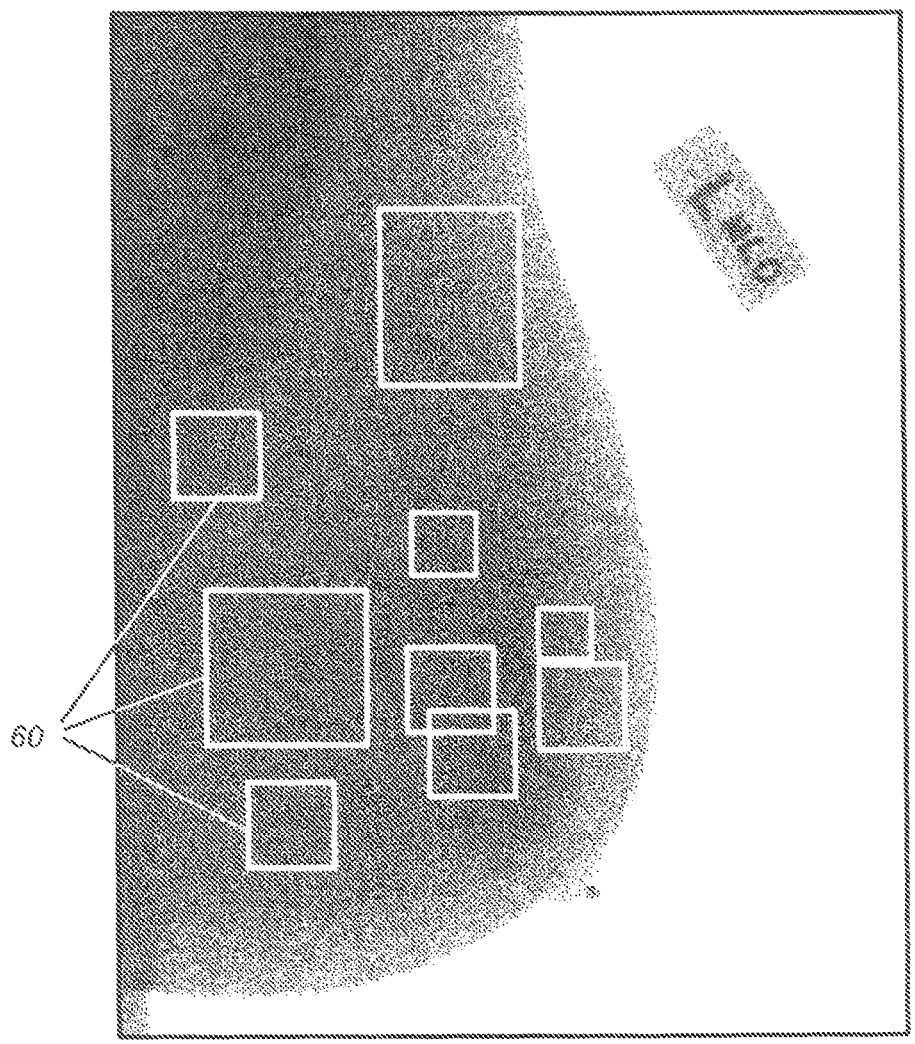
FIG. 4 shows a number of ROIs located on a breast image.
Figure 5:
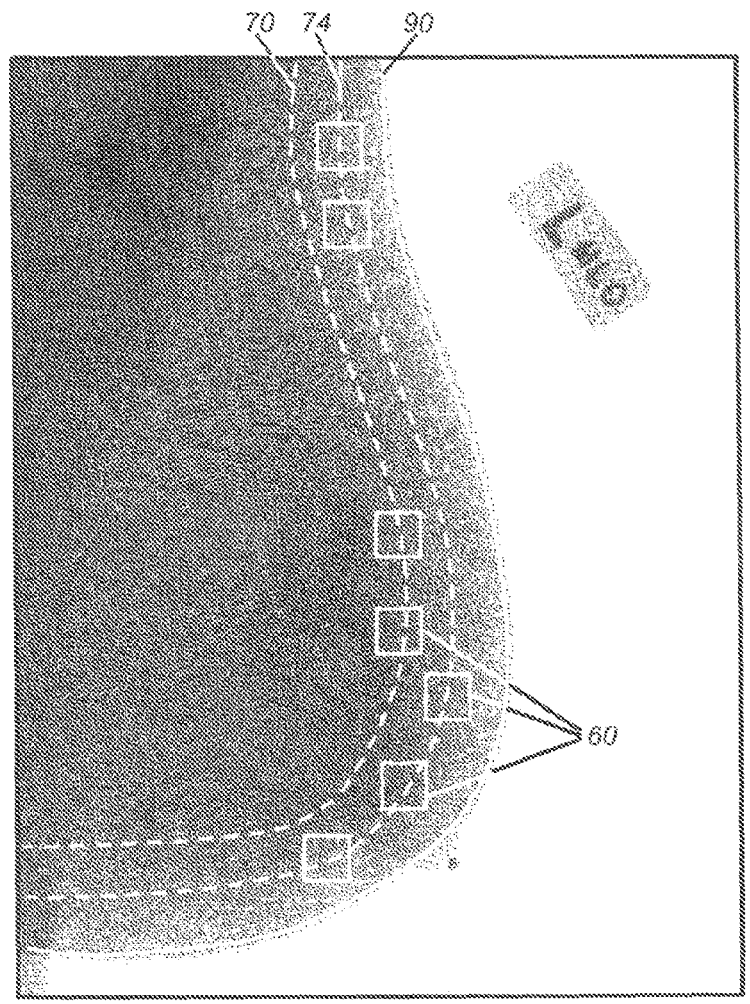
FIG. 5 shows a scheme for ROI distribution on a breast image.

In general, ROIs are preferably non-overlapping. ROIs 60 can be arbitrarily distributed in the breast region, as shown in FIG. 4, or may be assigned based on a certain guidelines. For example, FIG. 5 illustrates an example of locating ROIs in the breast region. In this example, a breast region contour 90 is extracted and used as a reference. Based on this reference, a set of contour segments (for example, 70 and 74) are generated within the breast region, substantially parallel to breast region contour 90, with pre-defined distances from contour segments 70 and 74 to reference breast region contour 90. With the assistance of these parallel contours, a number of ROIs 60 are arranged by setting the center of each ROI 60 along the contours, with a pre-set distance between its neighbor ROIs. When arranged in this way, ROIs 60 provide a convenient way to subsample the image so that needed data for characterizing the breast can be obtained from just a small portion of the image.

The shapes of ROIs 60 can vary. For example, while ROIs 60 are shown in FIGS. 4 and 5 as being rectangular and square, ROIs can be triangular, polygonal, oval, circular, or any shape that fits within the breast region. Moreover, ROI size/shape can fixed or related to ROI characteristics. In one embodiment of the present invention, the shape and size of an ROI 60 are determined by the image appearance of the ROI. Characteristics such as data intensity values or high contrast data can be related to ROI shape and size, for example. In one arrangement, to size ROIs, each ROI 60 is grown from its center point (that is, its "seed"), with growth terminating when the variation of the intensities within the ROI reaches a pre-defined threshold. Different shapes can be chosen to fit the grown region. The best/preferred fitting shape is later assigned to the ROI. As a result, individual ROIs 60 can overlap each other or be totally separated, depending on growing criteria and performance requirements.

The number of ROIs 60 used can be preset or can be arbitrarily determined from the image. Theoretically, the more ROIs 60 that are used, the better the performance. However, using an excessively large number of ROIs 60 can require more time which might delay the process of classification. Therefore, the number of ROIs 60 can be determined empirically to taken into consideration both computational complexity and classification performance.

After locating ROIs 60 on the image (step 122), features computation step 124 (FIG. 3) calculates a set of features from the full set of ROIs 60. These features can include the average intensity, the variance of the intensities, the average gradient magnitude, other parameters capable of representing characteristics of ROIs 60, and the like.

When these features are obtained, a histogram is computed for each feature from a sampled portion of the image formed by combining all ROIs 60. Then, a feature vector is formed by grouping these feature histograms together.

Widely used in pattern recognition and in machine learning applications, a feature vector is an n-dimensional data structure that is formed to store two or more numerical characteristics or "features" that are associated with an image or portion of an image or other object to be classified. In essence, the feature vector limits the number of characteristics of an object that are needed in order to classify that object. Feature extraction algorithms then use feature vectors to recognize standard patterns or to characterize an image in other ways.

Figure 6:
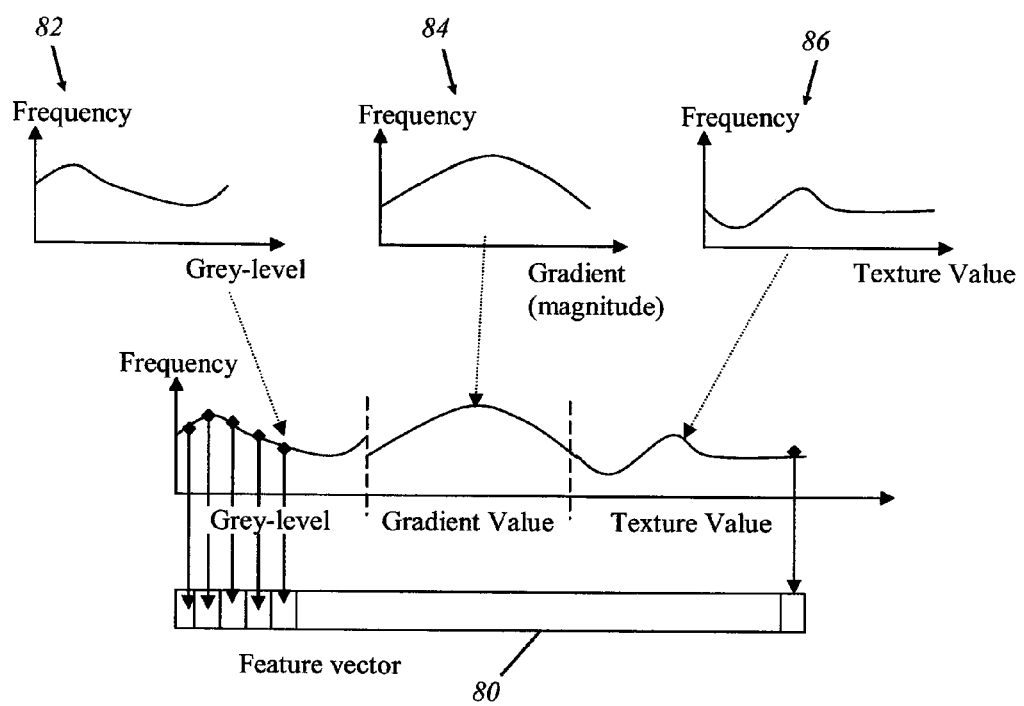
FIG. 6 shows components for forming of a feature vector according to one embodiment.

FIG. 6 shows an example for forming a feature vector 80 for an image as part of features computation step 124. First, three histograms are formed: a gray-level histogram 82, a gradient histogram 84, and a texture value histogram 86. Gray-level histograms 82, also termed intensity histograms, are a familiar type of histogram generated from an image and showing the frequency of each intensity data value. The gradient histogram 84 shows frequency data for gradient magnitude for an image and can be used in image processing as described, for example, in U.S. patent application No. 2004/0008901 entitled "Interpolated Image Filtering Method and Apparatus" by Avinash. As yet another example, U.S. patent application Publication No. 2006/0104532 entitled "Digital Imaging Processing Method" by Messina et al. also describes generation of a gradient histogram as part of image data transformation. Texture histogram 86 shows frequency data for texture values. Texture value calculation for each pixel in the ROI can be performed in any of a number of ways, using texture calculation techniques familiar to those skilled in the diagnostic imaging arts.

Values derived from these histograms are used to characterize the mammography image by forming feature vector 80. As is shown in FIG. 6, feature vector 80 stores data mapped from each of these types of histogram at a suitable resolution.

Thus, feature vector 80 can be a sizable data structure or array, depending on how it stores the frequency data from histograms 82, 84, and 86. In this way, the method of the present invention uses gray-level histogram 82, gradient histogram 84, and texture value histogram 86 to obtain statistical data from the set of ROIs obtained for each image. This information is used to represent the breast characteristics.

The use of histograms 82, 84, and 86 to obtain data and the generation of feature vector 80 as described with reference to FIG. 6 is one way to provide information for characterizing breast texture. The method of the present invention is not limited to use of this particular statistic type; other statistical parameters can also be used as long as they can capture important breast characteristics.

Figure 7A:
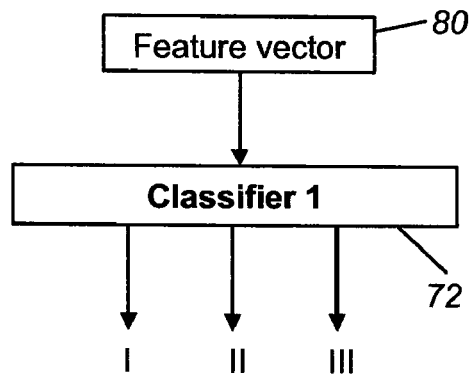
FIG. 7A shows the use of a single trained classifier for identifying breast type.
Figure 7B:
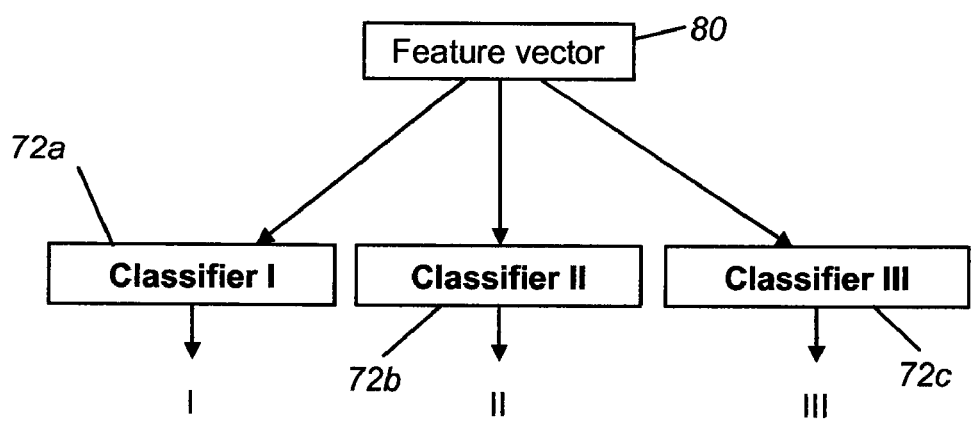
FIG. 7B shows the use of multiple trained classifiers for identifying breast type.

Referring again to FIG. 2, classification step 130 performs the necessary breast density classification using feature vector 80 provided for an image. In one type of embodiment, a breast is identified as being one of three breast types. For this decision process, then, either one or three pre-trained classifiers can be used. As is represented in FIG. 7A, where a single classifier 72 is used, the single classifier is trained to identify three breast density types. As a result, three outputs are employed, and each output presents a confidence level that the input mammogram matches a specific breast density. Alternately, as shown in FIG. 7B, where three classifiers are used, each classifier is trained to classify one breast density type from all the others.

Methods for generating, training, and testing classifiers for feature vector 80 are well known in the image processing arts. During the training step, a collection of training images having known breast density information are used to train a classifier. The classifier can be of any of a number of type known in the art, such as a neural network, a support vector machine, or decision trees, for example. If the original features are not effective for classification, an optional step can be added for computing a suitable transformation from the original features. The benefit of this step is to further study the characteristics of training features and to derive the most discriminating features for classification. Examples of conventional transformations include normalization, feature extraction by principle component analysis (PCA) or by independent component analysis (ICA), or by a non-linear transformation to create secondary features. For more information on classifiers and feature extraction in the imaging arts, see Duda, Hart, and Stork, *Pattern Classification*, John Wiley & Sons, New York, 2001. In one embodiment of the present invention, PCA is performed on each feature histogram, and the resulting secondary features are then grouped together to form a new feature vector. Such a feature vector is later used for breast density type recognition.

Once the classifier is trained, a testing step is performed on a new set of images to evaluate the performance of classification. If the performance cannot satisfy the pre-set requirement, the classifier may be biased by, or over-fit, the training data. When this happens, the classifier can be retrained to perform on both training and testing data.

Because combined results are more likely to be accurate, it is a useful technique to preserve ambiguity data for individual checks until a classification decision can be made. To preserve the ambiguity of mammogram images, the present invention outputs a probability vector for each input mammogram image to represent its breast density. In the probability vector, each element corresponds to a pre-defined breast density type. The final decision is made by combining all mammograms of the same examination.

In a preferred embodiment of the present invention, the probability vectors of mammograms from an examination are summed together and the breast density type with the highest confidence sum assigned to all mammograms of the examination. For example, FIG. 8 illustrates an example of an examination, which includes the standard set of four mammograms for a patient. Each mammogram has a probability vector having three elements representing confidence levels for each of the three predefined breast density types respectively. Each image is first evaluated individually for type I, II, or III likelihood. The sum of the confidence levels of these four mammograms shows that type II has the highest value, so that type II in this example is chosen to be the breast type of these four mammograms.

As this example shows, individual images may tend to suggest other results. For example, the RCC view actually rates slightly higher probability for type I than for type II. However, the combined results from all views show that breast type for this patient is more likely to be type II than type I. It is noted that this assessment is based on probability. Effective training can improve the performance of the algorithm for breast type classification. The method of the present invention is directed to reducing error to low levels similar to or better than the results obtained by a skilled diagnostician.

The present invention is not limited to the methods described herein in order to identify breast density. Any algorithm of similar nature can be employed to achieve the optimal classification. One suitable method could be a Bayesian decision rule, for example.

Recognition results can be either displayed at the console interface along with the processed or unprocessed image, or stored as parameters in the image headers, for example, in DICOM format. The classification process of the present invention can be carried out at the image acquisition device, following image capture, or at the workstation that is used to display the image for review and diagnosis by radiologists or physicians, or at some other logic processor apparatus. In one embodiment, one or more renderings of an image can be sent to a destination as a single entity rather than as individual images.

Results from the classification method of the present invention can be used in a number of ways. For example, knowing the breast type I, II, III, or IV classification can help to select appropriate parameters or models for image rendering, so that the resulting images provide the optimum diagnostic quality. The classification type can be reported to the radiologist, as an aid to improving diagnosis. Classification can be useful in monitoring breast density change for a patient over time and, if necessary, classification results can be used to provide a plot or other graphical description of breast density changes. Classification methods can be used as part of the analysis for mammogram image quality assurance.

The classification method of the present invention is not limited to x-ray mammography, but can be more broadly applied. This method can be extended to other diagnostic image modalities, such as Magnetic Resonance Imaging (MRI), and to ultrasound images of the breast or other tissue. Thus, what is provided is a method for automatically classifying breast density in mammograms to optimize the mammogram image rendering and assist diagnosis.

PARTS LIST

10 Display
12 Marker
20 RMLO image
30 LMLO image
34 Segmented image
40 RCC image
50 LCC image
60 ROI
70, 74 Contour segment
72, 72a, 72b, 72. Classifier
80 Feature vector
82 Gray-level Histogram
84 Gradient histogram
86 Texture value histogram
100 Image acquisition step
110 Segmentation step
115 Normalization step
120 Features identification step
122 ROI identification step
124 Features computation step
130 Classification step

What is claimed is:

1. A method for classifying tissue density of a breast, comprising:
    accessing mammography image data of the breast;
    segmenting the mammography image to identify a breast tissue region representing the breast tissue;
    identifying a plurality of regions of interest within the breast tissue region for obtaining image features therefrom;
    computing a plurality of image features from the identified plurality of regions of interest; and
    classifying the tissue density of the breast using the computed plurality of image features,
    wherein the step of identifying a plurality of regions comprises:
        extracting a contour of the breast tissue region;
        generating a plurality of contour segments substantially parallel to the breast tissue region contour and inside the breast tissue region; and
        defining a plurality of regions along the generated plurality of contour segments.

2. The method of claim 1 further comprising normalizing the breast tissue image content.

3. The method of claim 1 wherein computing a plurality of image features includes forming one or more of the following: a gray-value histogram, a gradient histogram, and a texture value histogram.

4. The method of claim 1 wherein classifying the tissue density further comprises generating a probability vector for the image, wherein each element in the probability vector represents a confidence level of a tissue density from each of said plurality of tissue density densities.

5. The method of claim 4 wherein the tissue density of a patient is determined according to the combination of probability vectors of a plurality of mammograms obtained for the patient in an examination.

6. The method of claim 1 further comprising displaying the classification results along with a mammography image.

7. The method of claim 1 further comprising storing the classification results along with the image data.

8. The method of claim 1 further comprising rendering one or more of the mammography images according to the classification of breast density type.

9. The method of claim 1 further comprising:
   determining tissue density classification for a patient at a first and second time period; and
   plotting the tissue density classification as a function of time.

10. The method of claim 1 wherein said generated plurality of contour segments are at pre-defined distances from the breast tissue region contour.

11. The method of claim 1 wherein each of said plurality of regions has a center and wherein the plurality of regions are arranged by setting the center of each region along a contour with a preset distance between neighboring regions.

12. The method of claim 1 including determining a shape and size of a particular region of interest based on the characteristics of the breast tissue within that particular region of interest.

13. The method of claim 1 wherein the step of computing the plurality of image features includes computing a feature vector from the statistics of image features obtained from the portion of image formed by combining all ROIs.

14. The method of claim 1 wherein the plurality of image features includes one or more of: pixel image intensity, gradient magnitude per pixel, and texture value per pixel.

* * * * *